US011505792B2

(12) United States Patent
Kong et al.

(10) Patent No.: US 11,505,792 B2
(45) Date of Patent: Nov. 22, 2022

(54) SITE-SPECIFIC INTEGRATION OF TRANSGENES

(71) Applicant: APPLIED STEMCELL, INC., Milpitas, CA (US)

(72) Inventors: Ling-jie Kong, Foster City, CA (US); Ruby Yanru Tsai, San Jose, CA (US)

(73) Assignee: APPLIED STEMCELL, INC., Milpitas, CA (US)

( * ) Notice: Subject to any disclaimer, the term of this patent is extended or adjusted under 35 U.S.C. 154(b) by 526 days.

(21) Appl. No.: 16/083,516

(22) PCT Filed: Apr. 11, 2017

(86) PCT No.: PCT/US2017/027073
§ 371 (c)(1),
(2) Date: Sep. 10, 2018

(87) PCT Pub. No.: WO2017/180669
PCT Pub. Date: Oct. 19, 2017

(65) Prior Publication Data
US 2019/0078076 A1 Mar. 14, 2019

Related U.S. Application Data

(60) Provisional application No. 62/320,863, filed on Apr. 11, 2016.

(51) Int. Cl.
*C12N 15/10* (2006.01)
*C12N 15/09* (2006.01)
(Continued)

(52) U.S. Cl.
CPC ............ *C12N 15/10* (2013.01); *C07H 21/04* (2013.01); *C12N 9/1211* (2013.01); *C12N 15/09* (2013.01);
(Continued)

(58) Field of Classification Search
CPC ...... C12N 15/10; C12N 9/1211; C12N 15/66; C12Y 207/01021
See application file for complete search history.

(56) References Cited

U.S. PATENT DOCUMENTS

2004/0265863 A1* 12/2004 Chesnut ................. C12N 15/66
435/325
2007/0184451 A1* 8/2007 Byrd ...................... C12N 15/70
435/5
(Continued)

FOREIGN PATENT DOCUMENTS

WO 2015/073703 A1 5/2015

OTHER PUBLICATIONS

Yau et al. "Less is more: strategies to remove marker genes from transgenic plants" (2013), BMC Biotech, 13:36 (Year: 2013).*
(Continued)

*Primary Examiner* — Teresa E Knight
(74) *Attorney, Agent, or Firm* — Jun He Law Offices P.C.; Yi Zhang (57) ABSTRACT

Provided is a method for knocking in a gene of interest to a cell. The genome of the cell contains a negative selectable marker, e.g., a thymidine kinase gene flanked by a pair of recombinase recognition sites (RRS), e.g., attP. The method involves introducing into the cell a targeting construct that contains a gene of interest flanked by a second pair of RRS, e.g., attB. The targeting construct also contains in the vector backbone a negative selectable marker, e.g., thymidine kinase gene. When a recombinase recognizing the RRS is expressed, the recombination events between the two pairs of RRS result in the site-specific integration of the gene of interest in the genome of the cell. Upon selection based on the negative selectable marker, the parental cells, cells with undesired integration, e.g., random integration, or the integration of the vector backbone are removed.

10 Claims, 2 Drawing Sheets

Specification includes a Sequence Listing.

(51) Int. Cl.
*C12N 15/63* (2006.01)
*C12N 15/64* (2006.01)
*C12N 15/90* (2006.01)
*C07H 21/04* (2006.01)
*C12N 9/12* (2006.01)
*C12N 15/11* (2006.01)
*C12N 15/66* (2006.01)

(52) U.S. Cl.
CPC ............ *C12N 15/102* (2013.01); *C12N 15/11* (2013.01); *C12N 15/63* (2013.01); *C12N 15/64* (2013.01); *C12N 15/66* (2013.01); *C12N 15/90* (2013.01); *C12N 15/907* (2013.01); *C12Y 207/01021* (2013.01)

(56) References Cited

U.S. PATENT DOCUMENTS

2012/0124686 A1 5/2012 Luo et al.
2014/0295501 A1 10/2014 Katona et al.

OTHER PUBLICATIONS

Chi et al. "A system for site-specific integration of transgenes in mammalian cells" (2019) PLosOne, 14(7): e0219842. (Year: 2019).*
Wang et al. "An Improved Single-Step Cloning Strategy Simplifies the Agrobacterium tumefacients-Mediated Transformation (ATMT)-Based Gene-Disruption Method for Verticillium dahliae" (2016), Phytopathology, vol. 106, No. 6: 645-652. (Year: 2016).*
Caron et al., "The human transcriptome map: clustering of highly expressed genes in chromosomal domains" Science (2001) 291(5507):1289-1292.
Esposito et al., "The integrase family of tyrosine recombinases: evolution of a conserved active site domain" Nucleic Acids Res. (1997) 25(18): 3605-3614.
Grindley et al., "Mechanisms of site-specific recombination" Annu. Rev. Biochem. (2006) 75: 567-605.
Keown et al., "Methods for introducing DNA into mammalian cells" Methods Enzymol. (1990) 185:527-537.
Munes-Duby et al., "Similarities and differences among 105 members of the Int family of site-specific recombinases" Nucleic Acids Res. (1998) 26(2): 391-406.
Stark et al., "Catalysis by site-specific recombinases" Trends Genet. (1992) 8(12): 432-439.
Zhou et al., "Genome-wide identification of chromosomal regions of increased tumor expression by transcriptome analysis" Cancer Res. (2003) 63(18):5781-5784.
International Search Report for PCT/US2017/027073, dated Jul. 10, 2017.
Sathiya N. Manivannan et al., "Targeted Integration of Single-Copy Transgenes in *Drosophila melanogaster* Tissue-Culture Cells Using Recombination-Mediated Cassette Exchange", Genetics, Oct. 20, 2015, No. 4, vol. 201, pp. 1319-1328.
The first office action and search report of the corresponding Chinese application 201780012763.X, dated May 10, 2021.

* cited by examiner

SITE-SPECIFIC INTEGRATION OF TRANSGENES

CROSS REFERENCE TO RELATED APPLICATIONS

This application is a national phase stage of international application PCT/US2017/027073, filed Apr. 11, 2017, which relates to and claims priority benefits from U.S. Provisional Patent Application No. 62/320,863, filed Apr. 11, 2016, the disclosure of which is hereby incorporated herein by reference.

FIELD OF THE INVENTION

The present invention generally relates to methods for integrating transgenes into a specific genomic locus in a cell.

BACKGROUND

Site-specific integration (i.e., knock-in) of a transgene into the chromosome of a mammalian cell is a technology that has broad applications in basic and applied biology. A typical process for site-specific integration involves the steps of 1) introducing a targeting vector containing a gene of interest into mammalian cells and 2) screening and selecting transfected cells with integration of the gene of interest at specific genomic locus. The efficiency of integration at a specific genomic locus is usually very low, and the screening and selection process is usually achieved by single cell cloning which is time consuming and labor intensive. In addition, the integration of the gene of interest together with the vector backbone DNA in the genome often leads to unwanted effects, such as the silencing of the gene of interest. Therefore, there is a continuing need to develop methods that can speed up the knock-in process and generate cells that do not contain the integration of the backbone DNA of the targeting vector.

SUMMARY

In one aspect, the present disclosure provides a method for inserting a transgene of interest into the genome of a cell. In one embodiment, the method comprises the step of introducing a targeting construct into a cell whose genome comprises a landing pad. The landing pad comprises sequentially (i) a first recombinase recognition site (RRS), (ii) a first negative selectable marker, and (iii) a second RRS. The targeting construct comprises (a) an exchange cassette and (b) a selectable cassette. The exchange cassette comprises sequentially (i) a third RRS, (ii) the transgene of interest, and (iii) a fourth RRS. The selectable cassette comprises a second negative selectable marker. The method further comprises the step of expressing a site-specific recombinase in the cell, wherein the site-specific recombinase recognizes at least the first and the third RRS. The cell is then maintained under a condition that facilitates recombination between the first and the third RRS, and between the second and the fourth RRS, wherein at least the recombination between the first and the third RRS is mediated by the site-specific recombinase. Cells with site-specific integration of the transgene are selected.

In certain embodiments, the landing pad is located in the genome of the cell at a region of increased gene expression (RIDGE). Examples of the RIDGE include, without limitation, a Hipp11 (H11) locus, a ROSA26 locus and a AAVS1 locus.

In certain embodiments, the targeting construct can be liner or circular.

In certain embodiments, the first negative selectable marker can be the same as the second negative selectable marker. In certain embodiments, the first and the second negative selectable marker can be different. In certain embodiments, the first or the second negative selectable marker is a thymidine kinase gene.

In certain embodiments, the landing pad further comprises a positive selectable marker. In certain embodiments, the positive selectable marker is an aminoglycoside phosphotransferase gene (neomycin resistance gene), a puromycin-N-acetyl transferase (puromycin resistance gene) or a blasticidin S deaminase (blasticidin S resistance gene), or hygromycin B phosphotransferase gene (hygromycin resistance gene).

In certain embodiments, the first RRS is the same as the second RRS. In certain embodiments, the first RRS is different from the second RRS. In certain embodiments, the third RRS is the same as the fourth RRS. In certain embodiments, the third RRS is different from the fourth RRS. In certain embodiments, each of the first, the second, the third and the fourth RRS is independently selected from the group consisting of attB, attP, FRT, loxP, mutants thereof and tandem repeats thereof.

In certain embodiments, the site-specific recombinase is selected from the group consisting of Cre, Flp, the lambda integrase, gamma-delta resolvase, Tn3 resolvase, Sin resolvase, Gin invertase, Hin invertase, Tn5044 resolvase, IS607 transposase, Bxb1, wBeta, BL3, phiR4, A118, TG1, MR11, phi370, SPBc, TP901-1, phiRV, FC1, K38, phiBT1 and phiC31.

In certain embodiments, the recombination between the second and the fourth RRS is mediated by a second site-specific recombinase.

In certain embodiments, the landing pad further comprises a sequence encoding the site-specific recombinase.

In certain embodiments, the cell is a mammalian cell. In certain embodiments, the cell is a rodent cell. In certain embodiments, the cell is a human cell. In certain embodiments, the cell is an embryonic stem cell or a zygote.

In certain embodiments, the selecting step comprises exposing the cell to a selective agent. In certain embodiments, the selective agent is ganciclovir.

In another aspect, the present disclosure provides an isolated cell, the cell comprising a landing pad located at a RIDGE in the genome of the cell. The landing pad comprises sequentially (i) a first RRS, (ii) a negative selectable marker, and (iii) a second RRS. In certain embodiments, the landing pad further comprises a positive selectable marker. In certain embodiments, the landing pad further comprises a polynucleotide sequence encoding a site-specific recombinase that recognizes at least the first or the second RRS. In certain embodiments, the first and the second RRS are phiC31 attP (SEQ ID NO: 1).

In yet another aspect, the present disclosure provides a nucleic acid construct comprising (a) an exchange cassette and (b) a selectable cassette. The exchange cassette comprises sequentially (i) a first RRS, (ii) the transgene of interest, and (iii) a second RRS. The selectable cassette comprises a negative selectable marker. In certain embodiments, the first and the second RRS are phiC31 attB (SEQ ID NO: 2).

These and other features, aspects, and advantages of the present invention will become better understood with regard to the following description, appended claims and accompanying drawings.

BRIEF DESCRIPTION OF THE FIGURES

FIG. 2 shows an exemplary landing pad in a safe harbor locus in the genome of a cell. The landing pad contains a puromycin resistance gene fused to a thymidine kinase gene through T2A coding sequence, which is then linked to a phiC31 integrase gene via IRES. The puromycin resistance gene, the thymidine kinase gene and the phiC31 integrase gene are flanked by phiC31 recognition site, attP.

DESCRIPTION OF THE INVENTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Definition

As used herein, the singular forms "a", "an" and "the" include plural references unless the context clearly dictates otherwise.

A "cell", as used herein, can be prokaryotic or eukaryotic. A prokaryotic cell includes, for example, bacteria. A eukaryotic cell includes, for example, a fungus, a plant cell, and an animal cell. The types of an animal cell (e.g., a mammalian cell or a human cell) includes, for example, a cell from circulatory/immune system or organ (e.g., a B cell, a T cell (cytotoxic T cell, natural killer T cell, regulatory T cell, T helper cell), a natural killer cell, a granulocyte (e.g., basophil granulocyte, an eosinophil granulocyte, a neutrophil granulocyte and a hypersegmented neutrophil), a monocyte or macrophage, a red blood cell (e.g., reticulocyte), a mast cell, a thrombocyte or megakaryocyte, and a dendritic cell); a cell from an endocrine system or organ (e.g., a thyroid cell (e.g., thyroid epithelial cell, parafollicular cell), a parathyroid cell (e.g., parathyroid chief cell, oxyphil cell), an adrenal cell (e.g., chromaffin cell), and a pineal cell (e.g., pinealocyte)); a cell from a nervous system or organ (e.g., a glioblast (e.g., astrocyte and oligodendrocyte), a microglia, a magnocellular neurosecretory cell, a stellate cell, a boettcher cell, and a pituitary cell (e.g., gonadotrope, corticotrope, thyrotrope, somatotrope, and lactotroph)); a cell from a respiratory system or organ (e.g., a pneumocyte (a type I pneumocyte and a type II pneumocyte), a clara cell, a goblet cell, an alveolar macrophage); a cell from circular system or organ (e.g., myocardiocyte and pericyte); a cell from digestive system or organ (e.g., a gastric chief cell, a parietal cell, a goblet cell, a paneth cell, a G cell, a D cell, an ECL cell, an I cell, a K cell, an S cell, an enteroendocrine cell, an enterochromaffin cell, an APUD cell, a liver cell (e.g., a hepatocyte and Kupffer cell)); a cell from integumentary system or organ (e.g., a bone cell (e.g., an osteoblast, an osteocyte, and an osteoclast), a teeth cell (e.g., a cementoblast, and an ameloblast), a cartilage cell (e.g., a chondroblast and a chondrocyte), a skin/hair cell (e.g., a trichocyte, a keratinocyte, and a melanocyte (Nevus cell)), a muscle cell (e.g., myocyte), an adipocyte, a fibroblast, and a tendon cell), a cell from urinary system or organ (e.g., a podocyte, a juxtaglomerular cell, an intraglomerular mesangial cell, an extraglomerular mesangial cell, a kidney proximal tubule brush border cell, and a macula densa cell), and a cell from reproductive system or organ (e.g., a spermatozoon, a Sertoli cell, a leydig cell, an ovum, an oocyte). A cell can be normal, healthy cell; or a diseased or unhealthy cell (e.g., a cancer cell). A cell further includes a mammalian zygote or a stem cell which include an embryonic stem cell, a fetal stem cell, an induced pluripotent stem cell, and an adult stem cell. A stem cell is a cell that is capable of undergoing cycles of cell division while maintaining an undifferentiated state and differentiating into specialized cell types. A stem cell can be an omnipotent stem cell, a pluripotent stem cell, a multipotent stem cell, an oligopotent stem cell and a unipotent stem cell, any of which may be induced from a somatic cell. A stem cell may also include a cancer stem cell. A mammalian cell can be a rodent cell, e.g., a mouse, rat, hamster cell. A mammalian cell can be a lagomorpha cell, e.g., a rabbit cell. A mammalian cell can also be a primate cell, e.g., a human cell. In certain examples, the cells are those used for mass bioproduction, e.g., CHO cells.

It is noted that in this disclosure, terms such as "comprises", "comprised", "comprising", "contains", "containing" and the like have the meaning attributed in United States Patent law; they are inclusive or open-ended and do not exclude additional, un-recited elements or method steps. Terms such as "consisting essentially of" and "consists essentially of" have the meaning attributed in United States Patent law; they allow for the inclusion of additional ingredients or steps that do not materially affect the basic and novel characteristics of the claimed invention. The terms "consists of" and "consisting of" have the meaning ascribed to them in United States Patent law; namely that these terms are close ended.

The term "construct" or "nucleic acid construct" as used herein refers to a nucleic acid in which a polynucleotide sequence of interest is inserted into a vector.

The term "nucleic acid" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, shRNA, single-stranded short or long RNAs, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The term "introduce" in the context of inserting a nucleic acid sequence into a cell, means "transfection", or 'transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon. The construct of the present disclosure may be introduced into a cell using any method known in the art. Various techniques for transfecting animal cells may be employed, including, for example: microinjection, retrovirus mediated gene transfer, electroporation, transfection, or the like (see, e.g., Keown et al., Methods in Enzymology 1990, 185:527-537). In one embodiment, the construct is introduced to the cell via a virus.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

As used herein, "polynucleotide sequence of interest" refers to any nucleic acid fragment that one wishes to insert into a genome. Examples of nucleic acid fragments of interest include any gene (e.g., protein-encoding, miRNA-encoding, shRNA-encoding, ncRNA-encoding, etc), such as therapeutic genes, marker genes, control regions, trait-producing fragments, and like.

As used herein "promoter" includes reference to a region of DNA upstream from the start of transcription and involved in recognition and binding of RNA polymerase and other proteins to initiate transcription. Examples of promoters include without limitation CMV promoter, SV40 promoter, EF1A promoter, PGK promoter, etc.

As used herein, a "selectable marker" or "selection marker" refers a gene whose expression in cells allows the cells to be enriched or depleted under particular culture conditions. A selectable marker may be a foreign gene or a cellular gene which is not naturally expressed or such a gene which is naturally expressed, but at an inappropriate level, in the target cell populations. If the expression of the gene allows the cells to be enriched under particular conditions, the selectable marker is a "positive selectable marker." Typically, a positive selectable marker is a gene that encodes for antibiotic resistance and selecting for those cells that express the selection marker comprises introducing antibiotic into the culture. In use, application of the antibiotic selectively kills or ablates cells that do not express the marker, leaving behind a population of cells purified or enriched in respect of those expressing the antibiotic resistance. Examples of a positive selectable marker include aminoglycoside phosphotransferase (neomycin resistance gene), puromycin-N-acetyl transferase (puromycin resistance gene), hygromycin resistance gene, and blasticidin S deaminase (blasticidin S resistance gene). Other examples of positive selectable marker include genes that can be used to select through cell sorting, e.g., fluorescent proteins and cell surface markers. Conversely, if the expression of the gene allows the cells to be depleted under particular culture condition, the selectable marker is a "negative selectable marker." Examples of a negative selectable marker include thymidine kinase gene. In use, application of ganciclovir kills the cells with expression of thymidine kinase. Other examples of negative selectable markers include DT toxin, cell death genes, such as TRAIL, caspases and BCL2 family genes.

As used herein, the term "recombinase" or "site-specific recombinase" refers to a family of highly specialized enzymes that promote DNA rearrangement between specific target sites (Greindley et al., 2006; Esposito, D., and Scocca, J. J., Nucleic Acids Research 25, 3605-3614 (1997); Nunes-Duby, S. E., et al, Nucleic Acids Research 26, 391-406 (1998); Stark, W. M., et al, Trends in Genetics 8, 432-439 (1992)). Virtually all site-specific recombinases can be categorized within one of two structurally and mechanistically distinct groups: the tyrosine (e.g., Cre, Flp, and the lambda integrase) or serine (e.g, phiC31 integrase, gamma-delta resolvase, Tn3 resolvase and Gin invertase) recombinases. Both recombinase families recognize target sites composed of two inversely repeated binding elements that flank a spacer sequence where DNA breakage and religation occur. The recombination process requires concomitant binding of two recombinase monomers to each target site: two DNA-bound dimers (a tetramer) then join to form a synaptic complex, leading to crossover and strand exchange. "Hyper-active" forms of Tn3 resolvase containing activating mutations in Tn3 resolvase can catalyze strand exchange at a core site of 28bp without accessory sites, presumably through reconfiguration of the tertiary/quaternary structure of the tetramer.

The term "sequentially" when used to describe two polynucleotide sequences means that the two sequences are not overlap, while the first sequence can either locate at the upstream (5') or downstream (3') of the second sequence.

"Site-specific recombinase" as used herein refers to a family of enzymes that mediate the site-specific recombination between specific DNA sequences recognized by the enzymes. Examples of site-specific recombinase include, without limitation, Cre recombinase, Flp recombinase, the lambda integrase, gamma-delta resolvase, Tn3 resolvase, Sin resolvase, Gin invertase, Hin invertase, Tn5044 resolvase, Tn3 transposase, sleeping beauty transposase, IS607 transposase, Bxb1 integrase, wBeta integrase, BL3 integrase, phiR4 integrase, A118 integrase, TG1 integrase, MR11 integrase, phi370 integrase, SPBc integrase, TP901-1 integrase, phiRV integrase, FC1 integrase, K38 integrase, phiBT1 integrase and phiC31 integrase. In certain embodiments, the site-specific recombinase is a uni-directional recombinase. As used herein, "uni-directional recombinases" refer to recombinase enzymes whose recognition sites are destroyed after recombination has taken place. In other words, the sequence recognized by the recombinase is changed into one that is not recognized by the recombinase upon recombination mediated by the recombinase, and the continued presence of the recombinase cannot reverse the previous recombination event. Examples of uni-directional recombinase include, without limitation, phiC31 integrase and Bxb1 integrase.

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating.

Methods and Compositions for Site-Specific Integration

Figure 1:
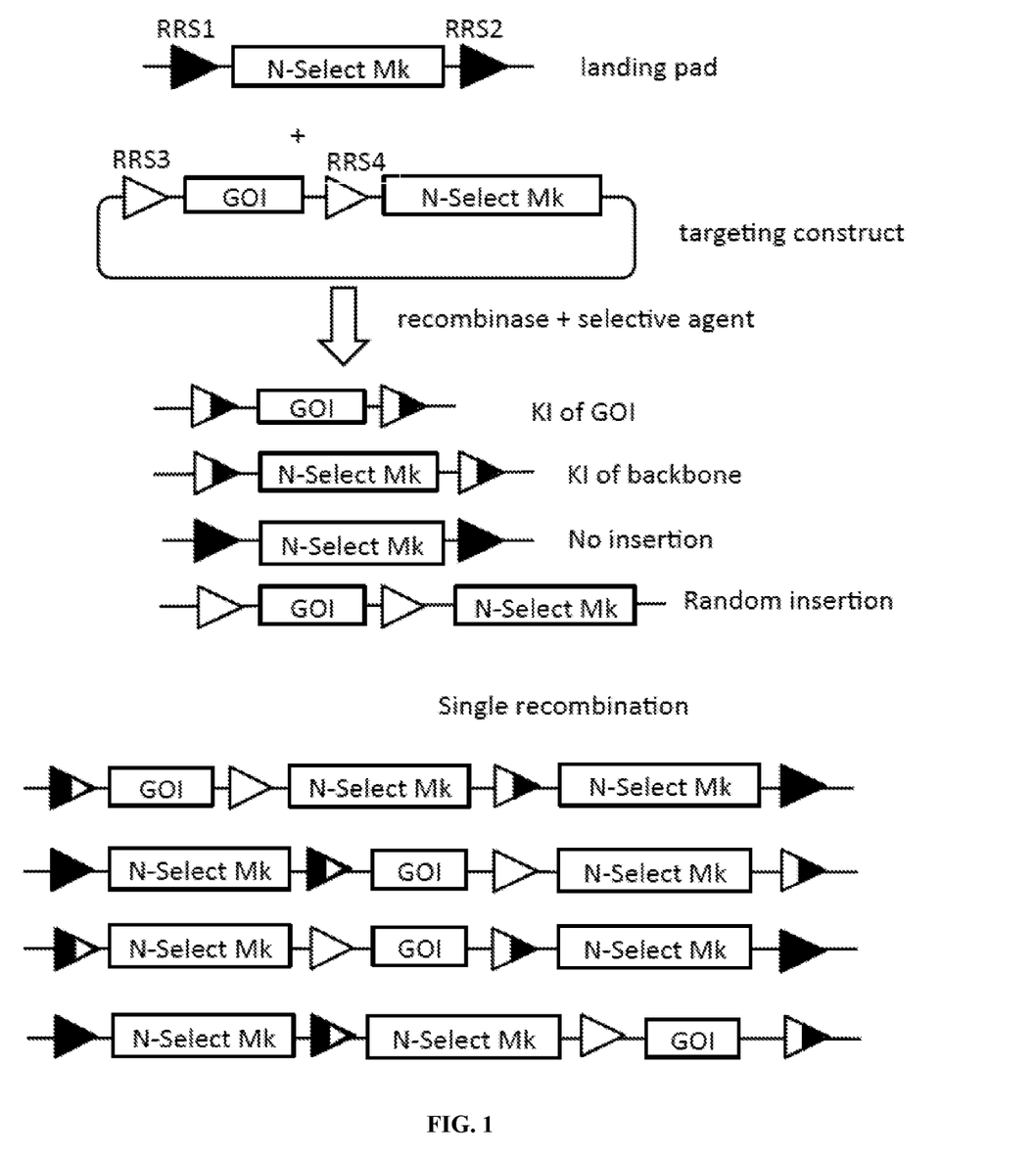
FIG. 1 is a schematic illustration of an exemplary method of site-specific integration of a gene of interest. The filled triangles represent RRS1 and RRS2 and the open triangles represent RRS3 and RRS4. The half-filled triangles represent hybrid RRS after recombination. GOI: Gene of interest. N-select Mk: negative selection marker. Only the KI of GOI cells survive the negative selection after recombination.

In one aspect, the present disclosure provides methods and compositions for inserting a polynucleotide sequence of interest into a specific genomic locus in a cell. FIG. 1 illustrates an exemplary example of the method for site-specific insertion of a polynucleotide sequence.

Referring to FIG. 1, the method involves introducing a targeting construct into a cell. The cell contains in a specific gnomic locus a landing pad, which contains sequences for recombination with the sequences in the targeting construct, thus directing the integration or "landing" of a heterologous polynucleotide sequence at the specific genomic locus. The landing pad includes a first negative selectable marker flanked by a pair of recombinase-recognition sites (RRS1 and RRS2). RRS1 can be the same as RRS2, or they can be different. The landing pad may contain additional elements between RRS1 and RRS2. In on embodiment, the landing pad contains a recombinase that recognizes at least RRS1 or RRS2.

In one embodiment, the negative selectable marker is viral thymidine kinase (TK). Thymidine kinase is an ATP-thymidine 5'-phosphotransferase that converts deoxythymidine into deoxythymidine 5'-monophosphate, which is further phosphorylated to deoxythymidine diphosphate and thereafter to deoxythymidine triphosphate by viral thymidine kinase and nucleoside diphosphate kinase respectively. Deoxythymidine triphosphate is incorporated into the synthesized DNA molecule by DNA polymerase. Some dNTP analogs, such as Ganciclovir (GCV), a synthetic analogue of 2'-deoxy-guanosine, have the ability to terminate the DNA synthesis upon their incorporation into synthesized DNA. Termination of synthesis triggers the apoptotic signaling cascades. While GCV is not recognized by mammalian thymidine kinase, it is recognized as a substrate for some viral thymidine kinase, such as Herpes Simplex Virus-1 thymidine kinase (HSV-TK). As a result, a mammalian cell expressing HSV-TK converts GCV into GCV phosphate, which is further phosphorylated and incorporated into the synthesized DNA, leading to the termination of synthesis and apoptosis.

In another embodiment, the negative selectable marker is cytosine deaminase. Cytosine deaminase hydrolyzes cytosine to uracil with release of ammonia. In physiological conditions, the modified site is recognized by endonucleases, then the phosphodiester bond in the DNA is broken, initiating repair by incorporation of a new cytosine. However, cytosine deaminase can also converts 5-fluorocytosine into 5-fluorouracil (5-FU). Therefore, upon provision of non-toxic prodrug 5-FC, cytosine deaminase converts it into highly toxic 5-FU (a suicide inhibitor of thymidylate synthetase), leading to the inhibition of cell growth and apoptosis.

In certain embodiments, the landing pad is located at a region of increased gene expression (RIDGE). RIDGEs have been genome-wide identified through transcriptome mapping where clusters of highly expressed genes reside therein (see, Zhou et al. 2003, Can. Res. 63:5781-5784; Caron et al., 2001, Science 291:1289-1292). Examples of RIDGE include Hipp11 (H11) locus, ROSA26 locus, AAVS1 and multiple antibiotic resistance (mar) locus.

The landing pad can be inserted in the cell using methods known in the arts. For example, the landing pad can be inserted to a specific genomic locus based on homologous recombination. In general, a construct containing the landing pad sequence flanked by sequences homologous to sequences in the specific genomic locus (homologous arm) is introduced into the cell. A double strand break or a nick in the specific genomic locus created by a site-specific nuclease, e.g., Cas9, TALEN, Zinc finger nuclease, can substantially increase the efficiency of homologous recombination. The construct may also contain a selectable marker, e.g., a positive selectable marker to facilitate the selection of the clones having homologous recombination. Therefore, in some embodiments, the landing pad may further contain a positive selectable marker.

In certain embodiments, the elements in the landing pad, such as the negative selectable marker is operably linked to a promoter. In certain embodiments, the landing pad also contains sequences or elements enhance the expression of the selectable marker or the recombinase, such as polyA sequence, T2A coding sequence, IRES (Internal Ribosome Entry Site), etc.

The targeting construct contains an exchange cassette comprising a gene of interest (GOI) flanked by a pair of RRS (RRS3 and RRS4). The vector backbone of the targeting construct contains a second negative selectable marker. In certain embodiments, the gene of interest or the second negative selectable marker is operably linked to a promoter. In certain embodiments, the gene of interest or the second negative selectable marker is operably linked to polyA sequences.

To facilitate the integration of the gene of interest, the landing pad and the targeting construct are configured so that in the presence of suitable site-specific recombinase, Recombination occurs between RRS1 and RRS3 and between RRS2 and RRS4. In certain embodiments, RRS1 and RRS3 are recognized by the same site-specific recombinase, and RRS2 and RRS4 are recognized by the same site-specific recombinase. In certain embodiments, RRS1 is the same as RRS2, and RRS3 is the same as RRS4. In such case, one site-specific recombinase mediates the recombination between RRS1 and RRS3 and the recombination between RRS2 and RRS4. In some embodiments, RRS1 and RRS2 have different sequences but can be recognized by the same site-specific recombinase, e.g., RRS2 is a variation of RRS1. In such cases, one site-specific recombinase can mediate the recombination between RRS1 and RRS3 and the recombination between RRS2 and RRS4. Because RRS1 and RRS2 have different sequences, recombination between RRS1 and RRS4 or recombination between RRS2 and RRS3 are avoided. In certain embodiments, two different site-specific recombinases mediate the recombination between RRS1 and RRS3 and the recombination between RRS2 and RRS4, respectively.

In certain embodiments, the expression of the site-specific recombinase can be achieved by inserting the recombinase gene into the genome of the cell. In one example, the recombinase gene is included in the landing pad. Alternatively, the expression of the site-specific recombinase can be achieved by introducing into the cell the recombinase protein, mRNA or a plasmid containing the recombinase gene.

When the targeting construct is introduced into the cell and the site-specific recombinase is expressed, a set of scenarios will occur. In a first possibility, two recombination events occur, one between RRS1 and RRS3 and the other between RRS2 and RRS4. As a result, the gene of interest is integrated to the specific genomic locus and replaces the negative selectable marker. In a second possibility, a recombination occurs between RRS1 and RRS4, and another recombination occurs between RRS2 and RRS3, resulting the negative selectable marker replacing the selectable marker in the landing pad. In a third possibility, there is no recombination or insertion happens, and the landing pad is intact. In a fourth possibility, the targeting construct is inserted randomly into the genome of the cell. In such case, the landing pad sequence will be intact, and the second negative selectable marker may be inserted into the genome. In a fifth possibility, the targeting construct may be inserted into the landing pad through one recombination event. Under this possibility, there are four possible outcomes outlined in FIG. 1. For example, if recombination occurs between RRS1 and RRS3, the first negative selectable marker will persist in the landing pad. Among all the above possibilities, the cells contain a negative selectable marker except in the first possibility, i.e., the gene of interest replaces the first negative selectable marker through two recombination events. In the presence of suitable selective agent, all the cells contain the negative selectable marker will be depleted. The cells with proper integration of the gene of interest will thus be selected.

Example

The following example describes an exemplary embodiment of the method for inserting a polynucleotide sequence of interest into a specific genomic locus in a cell. It is not intended to limiting in any manner.

Figure 2:
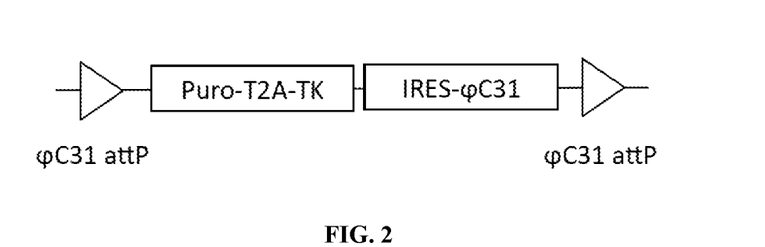

We used CRISPR-mediated homologous recombination to generate a master HEK293 cell line with a landing pad inserted in the ROSA26 locus. As illustrated in FIG. 2, the landing pad contains a puromycin resistant gene (Puro) linked to a thymidine kinase gene (TK) (SEQ ID NO: 3 for amino acid sequence of TK, SEQ ID NO:4 for nucleic acid sequence of TK) and through T2A self-cleaving peptide gene (T2A) (SEQ ID NO:7 for amino acid sequence of T2A and SEQ ID NO:8 for nucleic acid sequence of T2A). The landing pad also contains at the downstream of the Puro-T2A-TK fusion gene an IRES and a phiC31 integrase gene (SEQ ID NO: 5 for amino acid sequence of phiC31 integrase and SEQ ID NO:6 for nucleic acid sequence of phiC31 integrase). The Puro-T2A-TK fusion gene, IRES integrase gene are flanked by a pair of phiC31-recognition site, attP.

Figure 3:
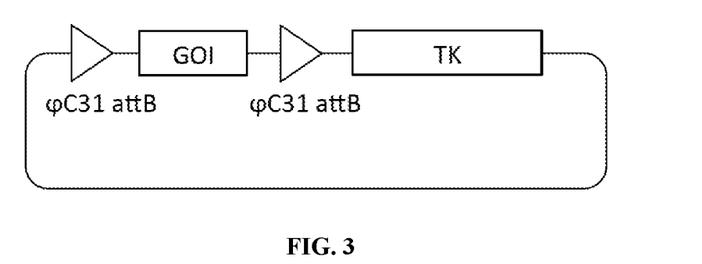
FIG. 3 shows an exemplary targeting construct that contains a gene of interest (GOI) flanked by two phiC31 attB sites and a thymidine kinase gene in the vector backbone.

We then transfected the master HEK293 cell line with a targeting construct as illustrated in FIG. 3. The targeting construct contains a GFP gene (GOI) flanked by a pair of phiC31-recognition site, attB. The targeting construct also contains a TK expression cassette in the backbone of the construct. The expression of the phiC31 integrase mediates the recombination between the attP and attB sites. The cells with high level expression of GFP were observed.

We then added ganciclovir to the mixture of the cells, the only cells can survive are the cells with Puro-TK-integrase cassette replaced by GFP gene via integrase mediated recombination. As a result, the cells with the GFP gene inserted at the ROSA26 locus are enriched, and the enriched cells do not contain the backbone sequence of the targeting construct.

What is claimed is:

1. A method for inserting a polynucleotide sequence of interest into a genome of a cell, the method comprising:
   introducing a targeting construct into the cell, wherein the cell contains in its genome a landing pad comprising sequentially
      (i) a first recombinase recognition site (RRS),
      (ii) a first negative selectable marker, and
      (iii) a second RRS, and
   the targeting construct comprises
      (a) an exchange cassette comprising sequentially
         (i) a third RRS,
         (ii) the polynucleotide sequence of interest, and
         (iii) a fourth RRS, and
      (b) a selectable cassette comprising a second negative selectable marker, wherein the second negative selectable marker locates outside of the exchange cassette on the target construct;
   expressing a site-specific recombinase in the cell, the site-specific recombinase recognizing at least the first and the third RRS;
   maintaining the cell under a condition that facilitates
      (a) a recombination between the first and the third RRS, and
      (b) a recombination between the second and the fourth RRS,
   wherein at least the recombination between the first and the third RRS is mediated by the site-specific recombinase; and
   selecting a site-specific integration of the polynucleotide sequence of interest into the genome of the cell.

2. The method of claim 1, wherein the landing pad is located at a region of increased gene expression (RIDGE).

3. The method of claim 2, wherein the RIDGE is Hipp11 (H11) locus, a ROSA26 locus or a AAVS1 locus.

4. The method of claim 1, wherein the first or the second negative selectable marker is a thymidine kinase gene.

5. The method of claim 1, wherein the landing pad further comprises a positive selectable marker.

6. The method of claim 5, wherein the positive selectable marker is an aminoglycoside phosphotransferase gene (neomycin resistance gene), a puromycin-N-acetyl transferase (puromycin resistance gene), a blasticidin S deaminase (blasticidin S resistance gene), or hygromycin B phosphotransferase gene (hygromycin resistance gene).

7. The method of claim 1, wherein the first and the second RRS are attP, and the third and the fourth RRS are attB.

8. The method of claim 1, wherein the recombination between the second and the fourth RRS is mediated by a second site-specific recombinase.

9. The method of claim 1, wherein the landing pad further comprises a sequence encoding the site-specific recombinase.

10. The method of claim 1, wherein the first and the second RRS are attB, and the third and the fourth RRS are attP.

\* \* \* \* \*

SEQUENCE LISTING

```
<160> NUMBER OF SEQ ID NOS: 8

<210> SEQ ID NO 1
<211> LENGTH: 70
<212> TYPE: DNA
<213> ORGANISM: Artificial Sequence
<220> FEATURE:
<223> OTHER INFORMATION: Synthesis

<400> SEQUENCE: 1
gttttcggga gtagtgcccc aactggggta acctttgagt tctctcagtt gggggcgtag      60
ggtcgccgac                                                            70

<210> SEQ ID NO 2
<211> LENGTH: 275
<212> TYPE: DNA
<213> ORGANISM: Artificial Sequence
<220> FEATURE:
<223> OTHER INFORMATION: Synthesis
```

```
<400> SEQUENCE: 2
cgatgtaggt cacggtctcg aagccgcggt gcgggtgcca gggcgtgccc ttgggctccc      60
cgggcgcgta ctccacctca cccatctggt ccatcatgat gaacgggtcg aggtggcggt     120
agttgatccc ggcgaacgcg cggcgcaccg ggaagccctc gccctcgaaa ccgctgggcg     180
cggtggtcac ggtgagcacg ggacgtgcga cggcgtcggc gggtgcggat acgcggggca     240
gcgtcagcgg gttctcgacg gtcacggcgg gcatg                                275

<210> SEQ ID NO 3
<211> LENGTH: 376
<212> TYPE: PRT
<213> ORGANISM: Artificial Sequence
<220> FEATURE:
<223> OTHER INFORMATION: Synthesis

<400> SEQUENCE: 3

Met Ala Ser Tyr Pro Gly His Gln His Ala Ser Ala Phe Asp Gln Ala
1               5                   10                  15

Ala Arg Ser Arg Gly His Ser Asn Arg Thr Ala Leu Arg Pro Arg
                20                  25                  30

Arg Gln Gln Glu Ala Thr Glu Val Arg Pro Glu Gln Lys Met Pro Thr
            35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300
```

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
            325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
            355                 360                 365

Ala Arg Glu Met Gly Glu Ala Asn
        370                 375

<210> SEQ ID NO 4
<211> LENGTH: 1131
<212> TYPE: DNA
<213> ORGANISM: Artificial Sequence
<220> FEATURE:
<223> OTHER INFORMATION: Synthesis

<400> SEQUENCE: 4

```
atggcttcgt accccggcca tcaacacgcg tctgcgttcg accaggctgc gcgttctcgc      60
ggccatagca accgacgtac ggcgttgcgc cctcgccggc agcaagaagc cacggaagtc     120
cgcccggagc agaaaatgcc cacgctactg cgggtttata tagacggtcc ccacgggatg     180
gggaaaacca ccaccacgca actgctggtg gccctgggtt cgcgcgacga tatcgtctac     240
gtacccgagc cgatgactta ctggcgggtg ctgggggctt ccgagacaat cgcgaacatc     300
tacaccacac aacaccgcct cgaccagggt gagatatcgg ccggggacgc ggcggtggta     360
atgacaagcg cccagataac aatgggcatg ccttatgccg tgaccgacgc cgttctggct     420
cctcatatcg gggggaggc tgggagctca catgccccgc cccgggccct caccctcatc     480
ttcgaccgcc atcccatcgc cgccctcctg tgctacccgg ccgcgcggta ccttatgggc     540
agcatgaccc ccaggccgt gctggcgttc gtggccctca tcccgccgac cttgcccggc     600
accaacatcg tgcttggggc ccttccggag acagacaca tcgaccgcct ggccaaacgc     660
cagcgccccg cgagcggct ggacctggct atgctggctg cgattcgccg cgtttacggg     720
ctacttgcca atacggtgcg gtatctgcag tgcggcgggt cgtggcggga ggactgggga     780
cagctttcgg ggacggccgt gccgccccag ggtgccgagc cccagagcaa cgcgggccca     840
cgacccata tcggggacac gttatttacc ctgtttcggg ccccgagtt gctggccccc     900
aacggcgacc tgtataacgt gtttgcctgg gccttggacg tcttggccaa cgcctccgt     960
tccatgcacg tctttatcct ggattacgac caatcgcccg ccggctgccg ggacgccctg    1020
ctgcaactta cctccgggat ggtccagacc cacgtcacca ccccggctc cataccgacg    1080
atatgcgacc tggcgcgcac gtttgcccgg gagatgggg aggctaactg a             1131
```

<210> SEQ ID NO 5
<211> LENGTH: 612
<212> TYPE: PRT
<213> ORGANISM: Artificial Sequence
<220> FEATURE:
<223> OTHER INFORMATION: Synthesis

<400> SEQUENCE: 5

Met Asp Thr Tyr Ala Gly Ala Tyr Asp Arg Gln Ser Arg Glu Arg Glu
1               5                   10                  15

Asn Ser Ser Ala Ala Ser Pro Ala Thr Gln Arg Ser Ala Asn Glu Asp
            20                  25                  30

-continued

Lys Ala Ala Asp Leu Gln Arg Glu Val Glu Arg Asp Gly Arg Phe
                35                  40                  45

Arg Phe Val Gly His Phe Ser Glu Ala Pro Gly Thr Ser Ala Phe Gly
 50                  55                  60

Thr Ala Glu Arg Pro Glu Phe Glu Arg Ile Leu Asn Glu Cys Arg Ala
 65                  70                  75                  80

Gly Arg Leu Asn Met Ile Ile Val Tyr Asp Val Ser Arg Phe Ser Arg
                 85                  90                  95

Leu Lys Val Met Asp Ala Ile Pro Ile Val Ser Glu Leu Leu Ala Leu
                100                 105                 110

Gly Val Thr Ile Val Ser Thr Gln Glu Gly Val Phe Arg Gln Gly Asn
                115                 120                 125

Val Met Asp Leu Ile His Leu Ile Met Arg Leu Asp Ala Ser His Lys
    130                 135                 140

Glu Ser Ser Leu Lys Ser Ala Lys Ile Leu Asp Thr Lys Asn Leu Gln
145                 150                 155                 160

Arg Glu Leu Gly Gly Tyr Val Gly Gly Lys Ala Pro Tyr Gly Phe Glu
                165                 170                 175

Leu Val Ser Glu Thr Lys Glu Ile Thr Arg Asn Gly Arg Met Val Asn
                180                 185                 190

Val Val Ile Asn Lys Leu Ala His Ser Thr Thr Pro Leu Thr Gly Pro
    195                 200                 205

Phe Glu Phe Glu Pro Asp Val Ile Arg Trp Trp Arg Glu Ile Lys
    210                 215                 220

Thr His Lys His Leu Pro Phe Lys Pro Gly Ser Gln Ala Ala Ile His
225                 230                 235                 240

Pro Gly Ser Ile Thr Gly Leu Cys Lys Arg Met Asp Ala Asp Ala Val
                245                 250                 255

Pro Thr Arg Gly Glu Thr Ile Gly Lys Lys Thr Ala Ser Ser Ala Trp
                260                 265                 270

Asp Pro Ala Thr Val Met Arg Ile Leu Arg Asp Pro Arg Ile Ala Gly
    275                 280                 285

Phe Ala Ala Glu Val Ile Tyr Lys Lys Pro Asp Gly Thr Pro Thr
    290                 295                 300

Thr Lys Ile Glu Gly Tyr Arg Ile Gln Arg Asp Pro Ile Thr Leu Arg
305                 310                 315                 320

Pro Val Glu Leu Asp Cys Gly Pro Ile Ile Glu Pro Ala Glu Trp Tyr
                325                 330                 335

Glu Leu Gln Ala Trp Leu Asp Gly Arg Gly Arg Gly Lys Gly Leu Ser
                340                 345                 350

Arg Gly Gln Ala Ile Leu Ser Ala Met Asp Lys Leu Tyr Cys Glu Cys
                355                 360                 365

Gly Ala Val Met Thr Ser Lys Arg Gly Glu Glu Ser Ile Lys Asp Ser
    370                 375                 380

Tyr Arg Cys Arg Arg Arg Lys Val Val Asp Pro Ser Ala Pro Gly Gln
385                 390                 395                 400

His Glu Gly Thr Cys Asn Val Ser Met Ala Ala Leu Asp Lys Phe Val
                405                 410                 415

Ala Glu Arg Ile Phe Asn Lys Ile Arg His Ala Glu Gly Asp Glu Glu
                420                 425                 430

Thr Leu Ala Leu Leu Trp Glu Ala Ala Arg Arg Phe Gly Lys Leu Thr
    435                 440                 445

```
Glu Ala Pro Glu Lys Ser Gly Glu Arg Ala Asn Leu Val Ala Glu Arg
    450                 455                 460

Ala Asp Ala Leu Asn Ala Leu Glu Glu Leu Tyr Glu Asp Arg Ala Ala
465                 470                 475                 480

Gly Ala Tyr Asp Gly Pro Val Gly Arg Lys His Phe Arg Lys Gln Gln
                485                 490                 495

Ala Ala Leu Thr Leu Arg Gln Gln Gly Ala Glu Arg Leu Ala Glu
        500                 505                 510

Leu Glu Ala Glu Ala Pro Lys Leu Pro Leu Asp Gln Trp Phe Pro
    515                 520                 525

Glu Asp Ala Asp Ala Asp Pro Thr Gly Pro Lys Ser Trp Trp Gly Arg
530                 535                 540

Ala Ser Val Asp Asp Lys Arg Val Phe Val Gly Leu Phe Val Asp Lys
545                 550                 555                 560

Ile Val Val Thr Lys Ser Thr Thr Gly Arg Gly Gln Gly Thr Pro Ile
                565                 570                 575

Glu Lys Arg Ala Ser Ile Thr Trp Ala Lys Pro Pro Thr Asp Asp Asp
                580                 585                 590

Glu Asp Asp Ala Gln Asp Gly Thr Glu Asp Val Ala Ala Pro Lys Lys
            595                 600                 605

Lys Arg Lys Val
    610

<210> SEQ ID NO 6
<211> LENGTH: 1839
<212> TYPE: DNA
<213> ORGANISM: Artificial Sequence
<220> FEATURE:
<223> OTHER INFORMATION: Synthesis

<400> SEQUENCE: 6
atggatacct acgccggagc ctacgacaga cagagccggg agagagagaa cagcagcgcc      60
gccagccccg ccacccagag aagcgccaac gaggataagg ccgccgatct gcagagagag     120
gtggagaggg acggcggcag attcagattt gtgggccact tcagcgaggc ccctggcacc     180
agcgccttcg gcaccgccga gagacccgag ttcgagagaa tcctgaacga gtgtagggcc     240
ggcaggctga acatgatcat cgtgtacgac gtgtcccggt tcagcaggct gaaggtgatg     300
gacgccatcc ctatcgtgtc cgagctgctg ccctgggcg tgaccatcgt gtccacccag     360
gaaggcgtct ttagacaggg caacgtgatg gacctgatcc acctgatcat gaggctggac     420
gccagccaca aggagagcag cctgaagagc gccaagatcc tggacaccaa gaacctgcag     480
agggagctgg cgggctatgt gggcggcaag gcccctacg gcttcgagct ggtgtccgag     540
accaaggaga tcacccggaa cggcaggatg gtgaacgtgg tgatcaacaa gctggcccac     600
agcaccaccc ccctgaccgg cccttcgag tttgagcccg acgtgatcag gtggtggtgg     660
cgggagatca agacccacaa gcacctgcct ttcaagcccg cagccaggc cgccatccac     720 cccggcagca tcaccggcct gtgtaagaga atggacgccg acgccgtgcc caccagaggc     780
gagaccatcg gcaagaaaac cgccagcagc gcctgggacc ccgccaccgt gatgagaatc     840
ctgagggacc ctaggatcgc cggcttcgcc gccgaggtga tctacaagaa gaagcccgac     900
ggcaccccca ccaccaagat cgagggctac agaatccaga gagacccat cacccctgaga    960 cctgtgagc tggactgtgg ccctatcatc gagcctgccg agtggtacga gctgcaggcc    1020
tggctggacg gcagaggcag aggcaagggc ctgagcagag gccaggccat cctgagcgcc    1080
```

```
atggacaagc tgtactgtga gtgtggcgcc gtgatgacca gcaagagagg cgaggagagc    1140
atcaaggaca gctaccggtg ccggagaaga aaggtggtgg accccagcgc ccctggccag    1200
cacgagggca cctgtaatgt gagcatggcc gccctggaca agttcgtggc cgagcggatc    1260
ttcaacaaga tccggcacgc cgagggcgac gaggagaccc tggccctgct gtgggaggcc    1320
gccagaagat tcggcaagct gaccgaggcc cccgagaaga gcggcgagag ggccaacctg    1380
gtggccgaga gagccgacgc cctgaacgcc ctggaggagc tgtacgagga cagagccgcc    1440
ggagcctatg acggccctgt gggcaggaag cacttcagaa agcagcaggc cgccctgacc    1500
ctgagacagc agggcgccga ggaaagactg gccgagctgg aggccgccga ggcccctaag    1560
ctgcccctgg atcagtggtt ccccgaggat gccgacgccg accccaccgg ccccaagtcc    1620
tggtggggca gagccagcgt ggacgacaag agggtgttcg tgggcctgtt cgtggataag    1680
atcgtggtga ccaagagcac caccggcagg ggccagggca cccccatcga aagagagcc    1740 agcatcacct gggccaagcc tcccaccgac gacgacgagg atgacgccca ggacggcacc    1800
gaggacgtgg ccgcccctaa gaaaaagcgg aaagtgtga                           1839
```

```
<210> SEQ ID NO 7
<211> LENGTH: 18
<212> TYPE: PRT
<213> ORGANISM: Artificial Sequence
<220> FEATURE:
<223> OTHER INFORMATION: Synthesis

<400> SEQUENCE: 7

Glu Gly Arg Gly Ser Leu Leu Thr Cys Gly Asp Val Glu Glu Asn Pro
1               5                   10                  15

Gly Pro

<210> SEQ ID NO 8
<211> LENGTH: 54
<212> TYPE: DNA
<213> ORGANISM: Artificial Sequence
<220> FEATURE:
<223> OTHER INFORMATION: Synthesis

<400> SEQUENCE: 8
gagggcaggg gcagcctgct gacctgcggc gacgtggagg agaaccccgg cccc           54
```